United States Patent [19]

Spivack

[11] 4,196,117

[45] Apr. 1, 1980

[54] ALKYLATED 1,1'-BIPHENYL-2,2'-DIYL PHOSPHITES AND STABILIZED COMPOSITIONS

[75] Inventor: John D. Spivack, Spring Valley, N.Y.

[73] Assignee: Ciba-Geigy Corporation, Ardsley, N.Y.

[21] Appl. No.: 866,748

[22] Filed: Jan. 3, 1978

[51] Int. Cl.$^2$ .................. C07F 9/145; C08K 5/52
[52] U.S. Cl. .................. 260/45.7 PH; 106/177;
252/400 A; 260/45.8 R; 260/45.85 B; 260/799;
260/927 R; 260/936
[58] Field of Search .............. 260/45.8 R, 927 R, 936,
260/45.7 PH

[56] References Cited

U.S. PATENT DOCUMENTS

| | | | |
|---|---|---|---|
| 3,297,631 | 1/1967 | Bown et al. .................. | 260/45.95 D |
| 3,415,906 | 12/1968 | Shepard et al. .................. | 260/937 |
| 3,558,554 | 1/1971 | Kuriyama et al. ........... | 260/45.7 PH |
| 3,796,684 | 3/1974 | Dever et al. .................. | 260/45.8 R |
| 4,094,855 | 6/1978 | Spivack .................. | 260/45.8 R |

OTHER PUBLICATIONS

Kirpichnikov et al., Chem. Abs., vol. 73, 1970, 15657a.

*Primary Examiner*—Hosea E. Taylor
*Assistant Examiner*—R. A. White
*Attorney, Agent, or Firm*—Vincent J. Cavalieri

[57] ABSTRACT

Alkylated 1,1'-biphenyl-2,2'-diyl phosphiates are prepared by reacting alkylated 2,2'-biphenol with phosphorus trichloride in an organic solvent an then reacting the intermediate with an alcohol or a thiol. Said phosphites are useful as stabilizers of organic polymers and lubricating oils, especially as process stabilzers for polyolefins, polyesters and polycarbonates.

23 Claims, No Drawings

ALKYLATED 1,1'-BIPHENYL-2,2'-DIYL PHOSPHITES AND STABILIZED COMPOSITIONS

BACKGROUND OF THE INVENTION

Organic polymeric materials such as plastics and resins and lubricating and mineral oil are subject to thermal, oxidative and photodegradation. A great variety of stabilizers are known in the art for stabilizing various substrates. Their effectiveness varies depending on the causes of degradation and the substrate stabilized. During the course of this work it was discovered that stabilizers that are very effective long term antioxidants are relatively poor process stabilizers which require stabilization of the substrate, against thermal degradation for a short time but at a relatively high temperature. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

The phosphites of this invention possess an unusual combination of desirable properties as compared to the prior art phosphites which makes these compounds particularly effective and useful as stabilizers. The prior art discloses unhindered 2,2'-biphenylenephenylphosphite and 2,2'-methylene bis-(dialkylphenyl)-phenylphosphites (Chem. Abst. 68, 12597Q (1968), Chem. Abst. 73, 15657 A (1970), Chem. Abst. 75, 130242Q (1971) and Soviet Union Pat. Nos. 378,389 and 429,070). These compounds are said to be stabilizers of various polymers. However the phosphites of this invention are much more effective especially as process stabilizers for polyolefins and other substrates, both in preventing polymer chain scission as well as discoloration during high temperature processing.

DETAILED DISCLOSURE

This invention is directed to alkylated 1,1'-biphenyl-2,2'-diyl phosphites and to polymeric and non-polymeric organic materials stabilized with said phosphites. More specifically the phosphites of this invention can be represented by the formula

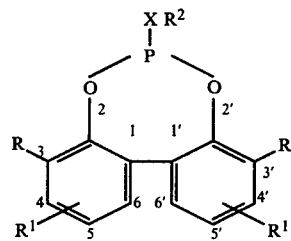

wherein

R is an alkyl group of 1 to 18 carbon atoms, $R^1$ is hydrogen or an alkyl group of 1 to 18 carbon atoms and $R^2$ is an alkyl group of 1 to 18 carbon atoms, phenyl, phenyl substituted with up to 3 alkyl groups each having 1 to 8 carbon atoms, or a group of the formula

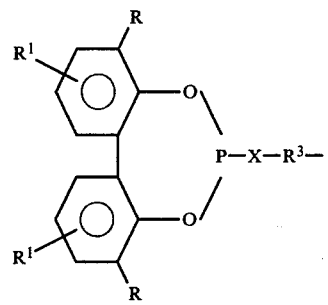

where $R^3$ is a divalent hydrocarbyl group selected from alkylene, arylene or allylene, and X is oxygen or sulfur.

The R groups are preferably straight-chain or branched alkyl with 1-8 carbon atoms, such as methyl, ethyl, n-propyl, iso-propyl, n-butyl, sec.-butyl, tert.-butyl, 2-ethylhexyl and n-octyl and tert-octyl. α-branched alkyl radicals with 3-8 carbon atoms are more preferred. The groups tert-butyl and tert-octyl are especially preferred. Also especially preferred is for the $R^1$ group to be in the para position to oxygen, particularly if $R^1$ is tert.-alkyl.

Although $R^1$ can be hydrogen or alkyl of 1 to 18 carbons, preferably it is an alkyl group of 1 to 8 carbon atoms, either straight-chain or branched-chain. Especially preferred is tert.-alkyl of 4 to 8 carbon atoms.

The group $R^2$ can be alkyl of 1 to 18 carbon atoms, such as methyl, ethyl, butyl, hexyl, heptyl, octyl, decyl, dodecyl, octadecyl and the like; or it can be phenyl or alkyl substituted phenyl, such as tolyl, xylyl, mesitylyl, ethylphenyl, butyl-phenyl, 3,5-dibutylphenyl, p-octylphenyl, 3,5-dioctylphenyl and the like. Preferably $R^2$ is a phenyl group having at least one brached alkyl group. Most preferably $R^2$ is 2-tert-butylphenyl, 2,4-di-tert-butyl-phenyl, 2,4,6-tri-tert-butylphenyl, 2-tert-butyl-5-methylphenyl, 2,6-di-tert-butyl-phenyl and 2,6-di-tert-butyl-4-methyl-phenyl, 2,4-di-tert-octylphenyl.

The $R^3$ group can be straight or branched chain alkylene of 1 to 12 carbon atoms or arylene of 6 to 30 carbon atoms.

Where it is alkylene it is preferably 2 to 6 carbon atoms, such as ethylene, propylene, trimethylene, butylene, tetramethylene, pentylene, hexamethylene, hexylene and the like. Where it is arylene it can be unsubstituted or substituted with 1 to 4 alkyl groups each alkyl having 1 to 8 and preferably 1 to 4 carbon atoms. Illustrative examples of arylene groups are phenylene, tolylene, 1,3,5-tri-methylphenylene, 1,2,4,5-tetramethylphenylene; 2,5-di-tert-butylphenylene, or the like. Arylene can also be a polynuclear arylene such as biphenylene or alkylenediphenylene where the alkylene has from 1 to 25 carbons, as for example, methylenediphenylene, isopropylenediphenylene and pentacosylenediphenylene. Most preferably $R^3$ is an alkylene of 2 to 6 carbons, phenylene or a phenyl substituted with one or two alkyl groups, each having 1 to 4 carbons.

The alkylated 1,1'-biphenyl-2,2'-diyl phosphites of this invention can be prepared by reacting an alkylated 2,2'-biphenol with phosphorus trichloride in a solvent to give the corresponding phosphorochloridite which in turn is reacted with an alkali metal alcoholate or phenolate to yield the desired product. The solvent is preferably aromatic, such as benzene, toluene, xylene and the like. A reaction temperature from room temperature to the reflux temperature of the reaction medium.

Another method for preparing the compounds of this invention involves reacting the phosphorochlordite with an appropriate alcohol or phenol optionally in the presence of a protan acceptor such as a tertiary amine, for example, triethylamine or pyridine.

The compounds of this invention are effective light stabilizers and/or antioxidants in a wide range of organic polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.
2. Mixtures of the homopolymers cited under (1), for example mixtures of polypropylene and polyethylene, polypropylene and polybutene-1, polypropylene and polyisobutylene.
3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene, with acrylic or methacrylic acid.
4. Polystyrene.
5. Copolymers of styrene and of α-methylstyrene, for example styrene/butadiene copolymers, styrene/acrylonitrile copolymers, styrene/acrylonitrile/methylacrylate copolymers, styrene/acrylonitrile/acrylic ester copolymers, styrene/acrylonitrile copolymers modified with acrylic ester polymers to provide impact strength as well as block copolymers, e.g., styrene/butadiene/styrene block copolymers.
6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.
8. Polymers which are derived from α,β-unsaturated acids and derivatives thereof, polyacrylates and polymethacrylates, polyacrylic amides and polyacrylonitrile.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide or the polymers which are derived from bis-glycidyl ethers.
11. Polyacetals, for example polyoxymethylene, as well as polyoxymethylenes which contain ethylene oxide as comonomer.
12. Polyalkylene oxides, for example polyoxyethylene, polypropylene oxide or polyisobutylene oxide.
13. Polyphenylene oxides.
14. Polyurethanes and polyureas.
15. Polycarbonates.
16. Polysulphones.
17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.
18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.
19. Cross-linked polymers which are derived from aldehydes on the one hand and from phenols, ureas and melamines on the other, for example phenol/formaldehyde, urea/formaldehyde and melamine/formaldehyde resins.
20. Alkyd resins, for example glycerol/phthalic acid resins and mixtures thereof with melamine/formaldehyde resins.
21. Unsaturated polyester resins which are derived from copolyesters of saturated and unsaturated dicarboxylic acids with polyhydric alcohols as well as from vinyl compounds as cross-linking agents and also the halogen-containing, flame-resistant modifications thereof.
22. Natural polymers, for example cellulose, rubber, as well as the chemically modified homologous derivatives thereof, for example cellulose acetates, cellulose propionates and cellulose butyrates and the cellulose ethers, for example methyl cellulose.

Compounds of this invention are particularly effective in stabilizing organic materials such as plastics, polymers, resins in addition to mineral and synthetic fluids such as lubricating oils, circulating oils, etc.

The compounds of this invention are particularly useful as stabilizers, especially for the protection of polyolefins, for instance, polyethylene, polypropylene, polyisobutylene, poly(butene-1), poly(pentene-1), poly(3-methylbutene-1), poly(4-methylpentene-1), various ethylene-propylene copolymers and the like.

Other substrates in which the compounds of this invention are particularly useful are polystyrene, including impact polystyrene, ABS resin, SBR, isoprene, as well as natural rubber, polyesters including polyethylene terephthalate and polybutylene terephthalate, including copolymers. Also stabilized are polyurethanes, polycarbonates, polyamides such as nylon 6, 6/6 and the like as well as copolyamides and polysulfones.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

Compounds of this invention stabilize polymers especially during high temperature processing with relatively little change in color, even though the polymer may undergo a number of extrusions. Among the polymers in which this property is especially apparent are polypropylene, polyethylene, styrenics such as ABS, polyethylene- and polybutylene-terephthalates, polycarbonates, natural rubber, synthetic rubber such as SBR. While many compounds which have been used as process stabilizers are sufficiently effective as process stabilizers for polyolefins only in the presence of costabilizers such as phenolic antioxidants, compounds of this invention are effective in the absence of phenolic antioxidants. Many of the compounds of this invention combine process stabilizing properties with the ability to confer light stability on the polymer. This is particularly important for polymer fibers where processing temperatures are among the highest and where stability to actinic light is a prime requirement. A particularly important property for stabilizers which are trivalent phosphorus esters is their non-hygroscopicity and resistance to hydrolysis in the presence of moisture in the atmosphere during ambient storage. Hygroscopicity frequently results in difficulty in incorporating the process stabilizer uniformly into the polymer causing stickiness and blockage during compounding, while hydrolysis of the phosphorus ester stabilizers during storage frequently results in compounds which are less effective.

The stabilizers of formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2.6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5 O-, N- and S-benzyl compounds, such as, for example, 3,5,3',5'-tetra-tert.-butyl-4,4'-dihydroxydibenzyl ether, octadecyl 4-hydroxy-3,5-dimethylbenzylmercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl]2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-(bis-β-(3,5-di-t-butyl-4-hydroxyphenyl)-propionyl)-hydrazine.

1.10 Esters of β-(3,5-di-tert.-butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.11 Esters of β-(5-tert.-butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol trimethylolethane, trimethylolpropane, tris-hydroxyethyl isocyanurate and 4-hydroxymethyl-1-phospha-2,6,7-trioxabicyclo[2,2,2]octane.

1.12 Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane, especially the tetra-bis ester of pentaerythritol.

1.13 Benzylphosphonates, such as, for example, dimethyl 3,5-di-tert.-butyl-4-hydroxybenzyl-phosphonate, diethyl 3,5-di-tert.-butyl-4-hydroxybenzyl-phosphonate, dioctadecyl 3,5-di-tert.-butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sect.octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1. 2-(2'-Hydroxyphenyl)-benzotriazoles, e.g. the 5'-methyl-, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2. 2,4-bis-(2'-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxycinnamic acid methyl ester or -butyl ester or N-(β-carbomethoxyvinyl)-2-methyl-indoline.

2.7. Sterically hindered amines, e.g. 4-benzoyl-2,2,6,6-tetramethylpiperidine, 4-stearyloxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4,5]decane-2,4-dione.

2.8. Oxalic acid diamides, e.g. 4,4'-di-octyloxy-oxanilide, 2,2'-di-octyloxy-5,5'-di-tert.-butyl-oxanolide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihyrazide, sebacic acid-bis-phenylhydrazide, bis-benzylidene-oxalic acid dihydrazide, N,N'-diacetal-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)hydrazine, N-salicyloyl-N'-salicylalhydrazine, 3-salicyloylamino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-palmitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-isodecyloxy-2,4,8,10-tetraoxa-3,9-diphospha[5,5]-undecane and tri-(4-hydroxy-3,5-di-tert.butylphenyl) phosphite.

Other additives that can be incorporated in the stabilized compositions are thiosynergists such as dilaurylthiodiproprionate or distearylthiodipropionate, lubricants such as stearyl alcohol fillers, carbon black, asbestos, kaolin, talc, glass fibers, pigments, optical brighteners, flameproofing agents and antistatic agents.

EXAMPLE 1

Preparation of (3,3',5,5'-tetra-tert.-butyl-1,1'-biphenyl-2,2'-diyl)phosphorochloride 45.21 grams of phosphorus trichloride in 50 ml of toluene was added dropwise over 85 minutes to a solution of 123.0 grams of 3,3',5,5'-tetra-tert.-butyl-2,2'-dihydroxy-1,1'-biphenyl and 60.6 grams of triethylamime in about 600 ml of toluene and stirred at room temperature overnight (about 20 hours). The reaction product was filtered free of triethylamine hydrochloride, the desired product being isolated by removal of the solvent at reduced pressure to yield a solid m.p. 168°–174°.

| Analysis | % Cl |
|---|---|
| Calcd. | 7.46 |
| Found | 7.50 |

EXAMPLE 2

O-(2,4-di-tert.-butylphenyl)-O$^1$, O$^2$-(3,3',5,5'-tetra-tert.-butyl-1,1'-biphenyl-2,2'-diyl)-phosphite 4.85 grams of 46.3% aqueous potassium hydroxide was added to a solution of 8.24 grams of 2,4-di-tert.-butylphenol in 250 ml of toluene and heated at reflux over a period of about 2 hours until all the water including reaction water was removed by azeotropic distillation yielding a dispersion of the potassium 2,4-di-tert.-butylphenolate in toluene. To this dispersion at −5° was added a solution of 21.7 grams of the compound of Example 1 in 60 ml of toluene at −5° to −3° over a period of 25 minutes and then stirring continued overnight. The reaction mixture was clarified by filtration of the precipitated potassium chloride and the product isolated as a residue by distillation of the toluene at reduced pressures. The product was isolated as crystals after crystallization from a solvent mixture of acetonitrile and toluene yielding white crystals melting at 195°–197°.

| Analysis: | % C | % H |
|---|---|---|
| Calcd. | 78.22 | 9.53 |
| Found | 78.56 | 9.86 |

EXAMPLE 3

O-2,6-di-tert.-butyl-4-methylpenyl)-O$^1$,O$^2$-(3,3',5,5'-tetra-tert.-butyl-1,1'-biphenyl-2,2'-diyl)phosphite The compound of this example was made by substantially the same method as Example 2 by reacting (4,4'-6,6'-tetra-tert.-butyl-2,2'-biphenylene)phosphorochlorodite with potassium 2,6-di-tert.-butyl-4-methylphenolate. After crystallization, the product is obtained as white crystals melting at 152°–155° C.

EXAMPLE 4

O-(2,4,6-tri-tert.-butylphenyl)-O$^1$,O$^2$-(3,3',5,5'-tetra-tert.-butyl-1,1'-biphenyl-2,2'-diyl)phosphite The compound of this example was made by substantially the same method as Example 2 by reacting 3,3',5,5'-tetra-tert.butyl-1,1'-biphenyl-2,2'-diyl) phosphorochlorodite with potassium 2,4,6-tri-tert. phenolate. After crystallization, the product is obtained as white crystals melting at 210°–212°.

EXAMPLE 5

O-iso-propyl-O$^1$,O$^2$,-(3,3',5,5'-tetra-tert.-butyl-1,1'-biphenyl-2,2'-diyl)

A solution of 23.75 grams of the chloridite of Example 1 in 80 ml of toluene was added dropwise at 15°–20° C. to 3.0 grams of isopropanol dissolved in 50.5 grams of triethylamine and stirring continued overnight at room temperature. After being filtered free of triethylamine hydrochloride and removal of volatiles at reduced pressures, the resulting residue was crystallized from isopropanol yielding the product as white crystals melting at 154°–156° C.

| Analysis: | % C | % H |
|---|---|---|
| Calcd. | 74.66 | 9.42 |
| Found | 74.34 | 9.73 |

EXAMPLE 6

S,S'(trimethylene)bis-(O,O$^1$(3,3'5,5'-tetra-tert.-butyl-1,1'-biphenyl-2,2'-diyl)thiophosphite)

The compound of this Example was made by the same procedure as Examples by reacting two molar proportions of tetra-3,3'5,5'-tert.butyl -1,1'-biphenyl-2,2'-diyl phosphorochloriditite (Example 1) with one molar proportion of 1,3-propanedithiol in the presence to triethylamine. After crystallization the product melted at 190°–193° C.

EXAMPLE 7

O,O'(4,4'-methylene-bis-(2,6-di-tert-butylphenylene))-O$^1$,O$^2$))3,3',5,5'-tetra-tert.-butyl-1,1'-biphenyl-1,1'-diyl)-phosphite)

The compound of this example is made by the same procedure as Example 5 by reacting two molar proportions of the chloridite of Example IV with one molar proportion of 4,4'-methylene-bis (2,6-di-tert.-butylphenol) in the presence of triethylamine.

EXAMPLE 8

O-n-octadecyl-O$^1$,O$^2$-(3,3',5,5'-tetra-tert-butyl-1,1'-biphenyl2,2'-diyl) phosphite The compound of this example was made by substantially the same procedure as Example 5 by reacting equimolar quantities of the chloridite of Example 1 with n-octadecanol in the presence of triethylamine. After purification by chromatography and by crystallization the product was obtained as white crystals melting at 38°–41° C.

Following the procedure of Example 5, the following compounds are prepared by reacting the appropriate starting materials.

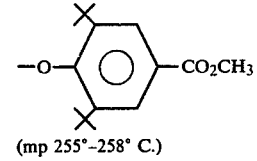

| Ex. No. | R | R$^1$ | X R$^2$ |
|---|---|---|---|
| 9 | (CH$_3$)$_3$C— | 4—(CH$_3$)$_3$C— | —OCH$_3$ (mp 190°–192° C.) |
| 10 | C$_8$H$_{18}$— | 4—CH$_3$— | —OC$_18$H$_{38}$ |
| 11* | (CH$_3$)$_3$C— | 4—(CH$_3$)$_3$C— | —O—⬡—CO$_2$CH$_3$ (with X substituents) (mp 255°–258° C.) |

-continued $$\text{[Structure: biphenyl with P-XR}^2\text{ bridged via two O atoms, with R substituents ortho to O and }R^1\text{ substituents on the rings]}$$

| Ex. No. | R | $R^1$ | $XR^2$ |
|---|---|---|---|
| 12 | $(CH_3)_3C-$ | $5-CH_3-$ | $-OC_8H_{18}$ |
| 13 | $(CH_3)_3C-$ | $4-(CH_3)_3C-$ | $-O-[\text{2,6-dimethylphenyl}]-CH_2$ (bracketed, subscript 2) |
| 14 | $(CH_3)_3C-$ | $4-(CH_3)_3C-$ | $-O-[\text{phenyl}]-C(CH_3)_2$ (bracketed, subscript 2) |
| 15** | $(CH_3)_3C-$ | $4-(CH_3)_3C-$ | $-OCH_2-C(CH_3)_2-CH_2O-$ (mp 165°–168° C.) |
| 16 | $(CH_3)_3C-$ | $r-(CH_3)_3C-$ | $-SC_8H_{17}$ |

*The alcohol used was methanol with the chloridate:alcohol ratio of 1:1
**The alcohol used was 2,2-dimethyl-1-1,3-propanediol with the chloridite:alcohol ratio of 2:1.

EXAMPLE 17

Processing Stability of Polypropylene at 500° F.

Base Formulation:

| | |
|---|---|
| Profax 6801 | 100 parts |
| Calcium stearate | 0.10 parts |

Stabilizers were solvent blended into polypropylene as solutions in methylene chloride and, after removal of the solvent by evaporation at reduced pressure, the resin was extruded using the following extruder conditions:

| | Temp. °F. | (°C.) |
|---|---|---|
| Cylinder #1 | 450 | 232 |
| Cylinder #2 | 475 | 246 |
| Cylinder #3 | 500 | 260 |
| Die #1 | 500 | 260 |
| Die #2 | 500 | 260 |
| RPM | 100 | |

During extrusion, the internal extruder pressure was determined using a pressure transducer. After each of the first, third and fifth extrusions, resin pellets were compression molded into 125 mil (3.2 mm) thick plaques at 380° F. (193° F.) and specimen yellowness index (Y.I.) determined according to ASTM D1925-63T.

The melt flow rate (MFR) was determined by ASTM method 1238 condition L. The melt flow rate varies directly as the transducer pressure and both are a measure of the molecular weight for a specific type of polymer.

The data is presented in Table I below.

Table 1

| Additive | (psi) Transducer Pressure After Ext. | | | ** MFR (g/10min) After Ext. | | | YI Color*** after Extrusion | | |
|---|---|---|---|---|---|---|---|---|---|
| | 1 | 3 | 5 | 1 | 3 | 5 | 1 | 3 | 5 |
| None | 1095 | 840 | 655 | 0.73 | 2.01 | 4.25 | 4.6 | 6.5 | 7.9 |
| 0.1 Antiox. A* | 1215 | 1045 | 930 | 0.42 | 1.04 | 1.25 | 6.7 | 8.6 | 10.5 |
| 0.15 Antiox. A* | 1270 | 1110 | 990 | 0.40 | 0.78 | 1.06 | 7.8 | 10.3 | 12.5 |
| The following contain 0.1% Antioxidant A and a compound as indicated below: | | | | | | | | | |
| 0.05 Cmpd.Ex.2 | 1260 | 1125 | 1035 | | | | 5.9 | 7.4 | 9.9 |
| 0.05 Cmpd.Ex.3 | 1250 | 1080 | 1020 | | | | 5.9 | 8.0 | 9.3 |
| 0.05 Cmpd.Ex.4 | 1230 | 1120 | 1010 | | | | 6.1 | 8.6 | 10.3 |
| 0.05 Cmpd.Ex.5 | 1380 | 1275 | 1200 | | | | 4.8 | 6.1 | 7.8 |
| 0.05 Cmpd.Ex.8 | 1350 | 1260 | 1170 | | | | 5.3 | 7.1 | 9.0 |
| 0.05 Cmpd.Ex.9 | 1335 | 1260 | 1200 | 0.19 | 0.24 | 0.36 | 5.4 | 6.6 | 8.5 |
| 0.05 Cmpd.Ex.6 | 1335 | 1260 | 1230 | 0.19 | 0.25 | 0.34 | 5.9 | 6.7 | 8.2 |
| 0.05 Cmpd.Ex.15 | 1375 | 1275 | 1230 | 0.20 | 0.24 | 0.31 | 5.7 | 7.1 | 8.1 |

Table 1-continued

| Additive | (psi) Transducer Pressure After Ext. | | | ** MFR (g/10min) After Ext. | | | YI Color*** after Extrusion | | |
|---|---|---|---|---|---|---|---|---|---|
| | 1 | 3 | 5 | 1 | 3 | 5 | 1 | 3 | 5 |
| 0.05 Cmpd.Ex.11 | 1245 | 1155 | 1080 | 0.27 | 0.38 | 0.56 | 5.9 | 7.4 | 8.5 |

*Antioxidant A is pentaerithritol tetrakis -[3-(3',5'-di-tert.-butyl-4-'-hydroxyphenyl) propionate]
**Melt flow rate
***Yellowness Index

What is claimed is:

1. A 1,1'-biphenylene phosphite of the formula

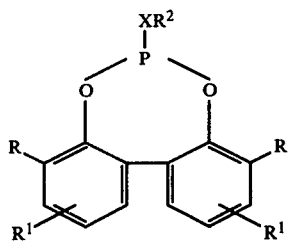

wherein
R is an alkyl group of 1 to 18 carbon atoms,
R$^1$ is hydrogen or an alkyl group of 1 to 18 carbon atoms and
R$^2$ is an alkyl group of 1 to 18 carbon atoms, phenyl, phenyl substituted with up to 3 alkyl groups each having 1 to 8 carbon atoms, or a group of the formula

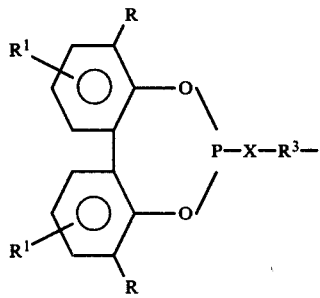

where R$^3$ is a divalent hydrocarbyl group selected from alkylene, arylene or allylene, and X is oxygen or sulfur.

2. A compound of claim 1 wherein
R is an α-branched alkyl radical of 3 to 8 carbon atoms,
R$^1$ is an alkyl of 1 to 8 carbon atoms
R$^2$ is a phenyl group having at least one branched alkyl group or a 1,1'-biphenylene phosphite group.

3. A compound of claim 2 wherein
R$^1$ is in the meta position to the R group.

4. A compound of claim 3 wherein
R is tert-butyl or tert-octyl,
R$^1$ is a tert-alkyl group of 4 to 8 carbon atoms,
R$^2$ is selected from the group consisting of 2-tert-butylphenyl, 2,4-di-tert-butyl-phenyl, 2,4,6-tri-tert-butylphenyl, 2-tert-butyl-5-methylphenyl, 2,6-di-tert-butyl-phenyl and 2,6-di-tert-butyl-4-methylphenyl, 2,4-di-tert-octylphenyl.

5. A compound of claim 4 wherein
R$^2$ is a group of the formula

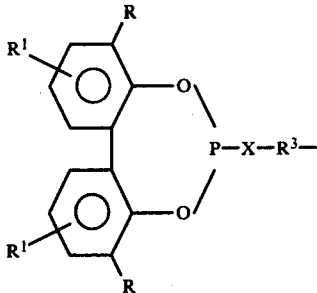

where
X is oxygen and
R$^3$ is an alkylene of 1 to 12 carbon atoms or arylene.

6. The compound of claim 1 which is O-(2,4-di-tert.-butylphenyl-O$^1$, O$^2$-3,3',5,5'-tetra-tert.-butyl-1,1'-biphenyl-2,2-diyl)phosphite.

7. The compound of claim 1 which is O-(2,6-di-tert.-butyl-4-methylphenyl)-O$^1$,O$^2$-(3,3',5,5'-tetra-tert.-butyl-1,1'-biphenyl-2,2'-diyl)phosphite.

8. The compound of claim 1 which is O-(2,2,6-tri-tert.-butylphenyl)O$^1$,O$^2$-3,3'5,5'-tetra-tert.-butyl-1,1'-biphenyl-2,2'-diyl)phosphite.

9. The compound of claim 1 which is O-Isopropyl-O$^1$,O$^2$-(3,3',5,5',-tetra-tert.-butyl-1,1'-biphenyl-2,2'-diyl)phosphite.

10. The compound of claim 1 which is S,S'(Trimethylene)bis-(O,O'-(3,3',5,5'-tetra-tert.-butyl-1,1'biphenyl2,2'-diyl)thiophosphite).

11. The compound of claim 1 which is O,O'(4,4'-methylene-bis-(2,6-di-tert.-butylphenylene)-O$^1$,O$^2$-(3,3',5,5'-tetra-tert.-butyl-1,1'-biphenyl-2,2'-diyl)-phosphite).

12. The compound of claim 1 which is O-(n-octadecyl-O$^1$,O$^2$-(3,3',5,5'-tetra-tert.-butyl-1,1'-biphenyl2,2'-diyl)phosphite.

13. The compound of claim 1 which is O-methyl-O$^1$,O$^2$-(3,3',5,5'-tetra-tert.-butyl-1,1'-biphenyl-2,2'-diyl)phosphite.

14. The compound of claim 1 which is O,O'(2,2-dimethylpropylene)-O$^1$,O$^2$-bis(3,3',5,5'-tetra-tert.-butyl-1,1'-biphenyl-2,2'-diyl)phosphite.

15. A composition of matter comprising an organic material subject to oxidative, thermal and actinic degradation stabilized with a compound of claim 1.

16. A composition of matter of claim 15 wherein the organic material is a synthetic polymer.

17. A composition of claim 16 wherein the polymer is a polyolefin homopolymer or copolymer.

18. A polyolefin homopolymer or copolymer stabilized with the compound of claim 10.

19. A composition of claim 17 stabilized with the compound of claim 13.

20. A composition of claim 17 stabilized with the compound of claim 14.

21. A composition of claim 17 stabilized with the compound of claim 9.

22. The compound of claim 1 which is O-ethyl-O$^1$,O$^2$-(3,3'5,5'-tetramethyl-1-1'-biphenyl-2,2'-diyl)phosphite.

23. The compound of claim 1 which is O-ethyl-O$^1$,O$^2$-(3,3',5,5'-tetra-tert.-butyl-1,1'-biphenyl-2,2'-diyl)phosphite.

* * * * *